(12) United States Patent
Ashforth et al.

(10) Patent No.: US 10,078,366 B2
(45) Date of Patent: Sep. 18, 2018

(54) HEAD-MOUNTABLE APPARATUS AND SYSTEM

(71) Applicant: Sony Interactive Entertainment Europe Limited, London (GB)

(72) Inventors: Jeremy David Ashforth, London (GB); Simon Mark Benson, London (GB); Simon John Hall, London (GB); Darren Myatt, London (GB)

(73) Assignee: Sony Interactive Entertainment Europe Limited (GB)

( * ) Notice: Subject to any disclaimer, the term of this patent is extended or adjusted under 35 U.S.C. 154(b) by 0 days.

(21) Appl. No.: 14/896,746

(22) PCT Filed: Jun. 11, 2014

(86) PCT No.: PCT/GB2014/051802
§ 371 (c)(1),
(2) Date: Dec. 8, 2015

(87) PCT Pub. No.: WO2014/199159
PCT Pub. Date: Dec. 18, 2014

(65) Prior Publication Data
US 2016/0187970 A1    Jun. 30, 2016

(30) Foreign Application Priority Data

Jun. 11, 2013  (GB) .................................. 1310364.3
Aug. 21, 2013  (GB) .................................. 1314972.9
Jun. 11, 2014  (GB) .................................. 1410425.1

(51) Int. Cl.
*G06F 3/01*        (2006.01)
*G02B 27/01*    (2006.01)
(Continued)

(52) U.S. Cl.
CPC .............. *G06F 3/012* (2013.01); *A61B 3/032* (2013.01); *A61B 3/113* (2013.01); *A63F 13/00* (2013.01);
(Continued)

(58) Field of Classification Search
None
See application file for complete search history.

(56) References Cited

U.S. PATENT DOCUMENTS 5,742,264 A    4/1998  Inagaki et al.
6,084,556 A *  7/2000  Zwern ................. G09B 21/008
                                                                    345/158
(Continued)

FOREIGN PATENT DOCUMENTS

EP    1731943 A1    12/2006
EP    1811493 A1    7/2007
(Continued)

OTHER PUBLICATIONS

International Search Report and Written Opinion for Application No. PCT/GB2014/051802 dated Aug. 18, 2014.
(Continued)

*Primary Examiner* — Kenneth B Lee, Jr.
(74) *Attorney, Agent, or Firm* — Lerner, David, Littenberg, Krumholz & Mentlik, LLP (57) ABSTRACT

A head mountable display (HMD) is provided that has a head motion detection function and one or more operations that depend upon detected head motion. Detected head motion is stored as motion data in memory. The way in which detected head motion is applied to a current operation depends upon the stored motion data. In one embodiment, the HMD includes a gaze detector configured to detect eye orientation of a user of the user so as to detect image regions at which the user is looking, and a detector configured to
(Continued)

detect item data indicative of items represented by the detected image regions.

18 Claims, 9 Drawing Sheets

(51) Int. Cl.
*A61B 3/113* (2006.01)
*A61B 3/032* (2006.01)
*A63F 13/00* (2014.01)

(52) U.S. Cl.
CPC ....... *G02B 27/017* (2013.01); *G02B 27/0172* (2013.01); *G02B 27/0179* (2013.01); *G06F 3/013* (2013.01); *G02B 2027/014* (2013.01); *G02B 2027/0187* (2013.01)

(56) References Cited

U.S. PATENT DOCUMENTS

| | | |
|---|---|---|
| 2005/0156817 A1 | 7/2005 | Iba |
| 2008/0276178 A1* | 11/2008 | Fadell .................. G02B 27/017 715/733 |
| 2010/0157433 A1 | 6/2010 | Mukawa et al. |
| 2010/0232727 A1* | 9/2010 | Engedal .................. G06T 7/251 382/285 |
| 2012/0143400 A1 | 6/2012 | Hinkel, III |
| 2012/0262558 A1 | 10/2012 | Boger et al. |
| 2013/0063477 A1 | 3/2013 | Richardson et al. |
| 2013/0128364 A1* | 5/2013 | Wheeler ................. A61B 3/113 359/630 |
| 2013/0246967 A1* | 9/2013 | Wheeler .............. G02B 27/017 715/784 |

FOREIGN PATENT DOCUMENTS

| | | |
|---|---|---|
| GB | 2501761 A | 11/2013 |
| WO | 02073287 A2 | 9/2002 |
| WO | 02086590 A1 | 10/2002 |

OTHER PUBLICATIONS

Search Report for Application No. GB1314972.9 dated Mar. 7, 2014.
Combined Search and Examination Report for Application No. GB1410425.1 dated Aug. 14, 2014.
Search Report for Application No. GB1314972.9 dated Feb. 6, 2014.
Search Report for Application No. GB1310364.3 dated Nov. 28, 2013.
Search Report for Application No. GB1310364.3 dated Dec. 20, 2013.
Examination Report for Application No. GB14732312.5, dated May 22, 2017.
Bajura et al., Dynamic Registration Correction in Augmented-Reality Systems, pp. 189-196, 1995.

* cited by examiner

| Image region | Item | Code |
|---|---|---|
| 810a | | |
| 810b | | |
| 810c | | |
| 810d | | |

HEAD-MOUNTABLE APPARATUS AND SYSTEM

CROSS REFERENCE TO RELATED APPLICATION

The present application is a national phase entry under 35 U.S.C. § 371 of International Application No. PCT/GB2014/051802, filed Jun. 11, 2014, published in English, which claims the benefit of and priority to GB Patent Application No. 1310364.3, filed Jun. 11, 2013 and GB Patent Application No. 1314972.9, filed Aug. 21, 2013, the entire disclosures of which are hereby incorporated by reference herein. The present application also claims the benefit of and priority to GB Patent Application No. 1410425.1, filed Jun. 11, 2014, the entire disclosure of which is hereby incorporated by reference herein.

BACKGROUND

Field of the Disclosure

This invention relates to head-mountable apparatus and systems.

Description of the Prior Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

A head-mountable display (HMD) is one example of a head-mountable apparatus. Audio headphones comprising a frame supporting one or more audio transducers are another example of a head-mountable apparatus. A head-mounted torch or light is a further example of a head-mountable apparatus. The following background discussions will relate mainly to HMDs, but the principles are also applicable to other types of head-mountable apparatus.

In an HMD, an image or video display device is provided which may be worn on the head or as part of a helmet. Either one eye or both eyes are provided with small electronic display devices.

Some HMDs allow a displayed image to be superimposed on a real-world view. This type of HMD can be referred to as an optical see-through HMD and generally requires the display devices to be positioned somewhere other than directly in front of the user's eyes. Some way of deflecting the displayed image so that the user may see it is then required. This might be through the use of a partially reflective mirror placed in front of the user's eyes so as to allow the user to see through the mirror but also to see a reflection of the output of the display devices. In another arrangement, disclosed in EP-A-1 731 943 and US-A-2010/0157433, a waveguide arrangement employing total internal reflection is used to convey a displayed image from a display device disposed to the side of the user's head so that the user may see the displayed image but still see a view of the real world through the waveguide. Once again, in either of these types of arrangement, a virtual image of the display is created (using known techniques) so that the user sees the virtual image at an appropriate size and distance to allow relaxed viewing. For example, even though the physical display device may be tiny (for example, 10 mm×10 mm) and may be just a few millimeters from the user's eye, the virtual image may be arranged so as to be perceived by the user at a distance of (for example) 20 m from the user, having a perceived size of 5 m×5 m.

Other HMDs, however, allow the user only to see the displayed images, which is to say that they obscure the real world environment surrounding the user. This type of HMD can position the actual display devices in front of the user's eyes, in association with appropriate lenses or other optical components which place a virtual displayed image at a suitable distance for the user to focus in a relaxed manner—for example, at a similar virtual distance and perceived size as the optical see-through HMD described above. This type of device might be used for viewing movies or similar recorded content, or for viewing so-called virtual reality content representing a virtual space surrounding the user. It is of course however possible to display a real-world view on this type of HMD, for example by using a forward-facing camera to generate images for display on the display devices.

Although the original development of HMDs was perhaps driven by the military and professional applications of these devices, HMDs are becoming more popular for use by casual users in, for example, computer game or domestic computing applications.

The foregoing paragraphs have been provided by way of general introduction, and are not intended to limit the scope of the following claims. The described embodiments, together with further advantages, will be best understood by reference to the following detailed description taken in conjunction with the accompanying drawings.

Various aspects and features of the present invention are defined in the appended claims and within the text of the accompanying description and include at least a head mountable apparatus such as a display and a method of operating a head-mountable apparatus as well as a computer program.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DESCRIPTION OF THE EMBODIMENTS

Figure 1:
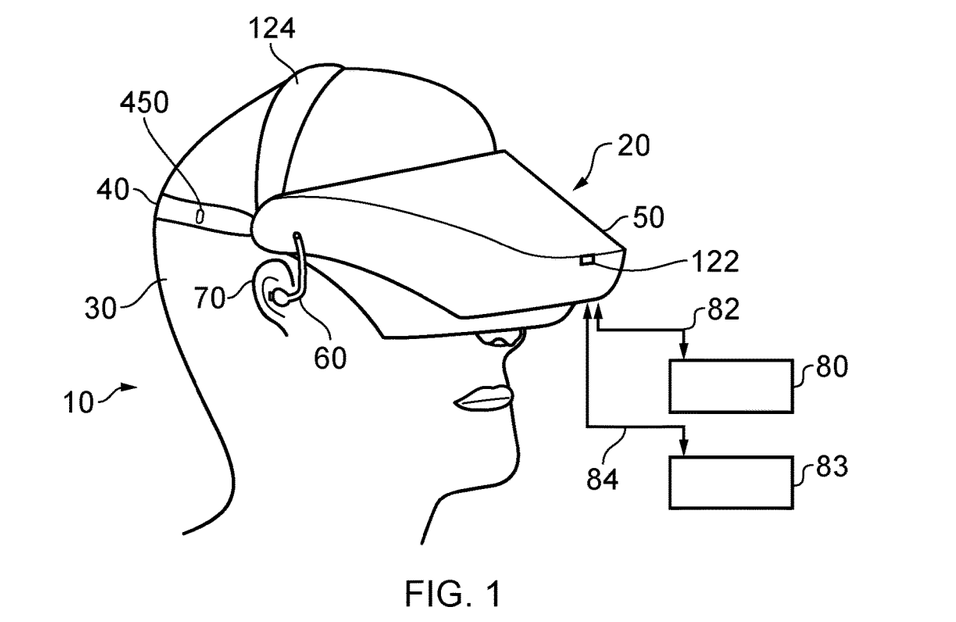
FIG. 1 schematically illustrates an HMD worn by a user.

Referring now to FIG. 1, a user 10 is wearing an HMD 20 (as an example of a generic head-mountable apparatus—other examples, where the technical context allows, including audio headphones or a head-mountable light source) on the user's head 30. The HMD comprises a frame 40, in this example formed of a rear strap and a top strap, and a display portion 50.

Note that the HMD of FIG. 1 may comprise further features, to be described below in connection with other drawings, but which are not shown in FIG. 1 for clarity of this initial explanation.

The HMD of FIG. 1 completely (or at least substantially completely) obscures the user's view of the surrounding environment. All that the user can see is the pair of images displayed within the HMD.

The HMD has associated headphone audio transducers or earpieces 60 which fit into the user's left and right ears 70. The earpieces 60 replay an audio signal provided from an external source, which may be the same as the video signal source which provides the video signal for display to the user's eyes.

The combination of the fact that the user can see only what is displayed by the HMD and, subject to the limitations of the noise blocking or active cancellation properties of the earpieces and associated electronics, can hear only what is provided via the earpieces, mean that this HMD may be considered as a so-called "full immersion" HMD. Note however that in some embodiments the HMD is not a full immersion HMD, and may provide at least some facility for the user to see and/or hear the user's surroundings. This could be by providing some degree of transparency or partial transparency in the display arrangements, and/or by projecting a view of the outside (captured using a camera, for example a camera mounted on the HMD) via the HMD's displays, and/or by allowing the transmission of ambient sound past the earpieces and/or by providing a microphone to generate an input sound signal (for transmission to the earpieces) dependent upon the ambient sound.

A front-facing camera 122 may capture images to the front of the HMD, in use. A Bluetooth® antenna 124 may provide communication facilities or may simply be arranged as a directional antenna to allow a detection of the direction of a nearby Bluetooth transmitter.

In operation, a video signal is provided for display by the HMD. This could be provided by an external video signal source 80 such as a video games machine or data processing apparatus (such as a personal computer), in which case the signals could be transmitted to the HMD by a wired or a wireless connection 82. Examples of suitable wireless connections include Bluetooth® connections. Audio signals for the earpieces 60 can be carried by the same connection. Similarly, any control signals passed from the HMD to the video (audio) signal source may be carried by the same connection. Furthermore, a power supply 83 (including one or more batteries and/or being connectable to a mains power outlet) may be linked by a cable 84 to the HMD. Note that the power supply 83 and the video signal source 80 may be separate units or may be embodied as the same physical unit. There may be separate cables for power and video (and indeed for audio) signal supply, or these may be combined for carriage on a single cable (for example, using separate conductors, as in a USB cable, or in a similar way to a "power over Ethernet" arrangement in which data is carried as a balanced signal and power as direct current, over the same collection of physical wires). The video and/or audio signal may be carried by, for example, an optical fibre cable. In other embodiments, at least part of the functionality associated with generating image and/or audio signals for presentation to the user may be carried out by circuitry and/or processing forming part of the HMD itself. A power supply may be provided as part of the HMD itself.

Some embodiments of the invention are applicable to an HMD having at least one electrical and/or optical cable linking the HMD to another device, such as a power supply and/or a video (and/or audio) signal source. So, embodiments of the invention can include, for example:

(a) an HMD having its own power supply (as part of the HMD arrangement) but a cabled connection to a video and/or audio signal source;

(b) an HMD having a cabled connection to a power supply and to a video and/or audio signal source, embodied as a single physical cable or more than one physical cable;

(c) an HMD having its own video and/or audio signal source (as part of the HMD arrangement) and a cabled connection to a power supply; or (d) an HMD having a wireless connection to a video and/or audio signal source and a cabled connection to a power supply.

If one or more cables are used, the physical position at which the cable 82 and/or 84 enters or joins the HMD is not particularly important from a technical point of view. Aesthetically, and to avoid the cable(s) brushing the user's face in operation, it would normally be the case that the cable(s) would enter or join the HMD at the side or back of the HMD (relative to the orientation of the user's head when worn in normal operation). Accordingly, the position of the cables 82, 84 relative to the HMD in FIG. 1 should be treated merely as a schematic representation.

Accordingly, the arrangement of FIG. 1 provides an example of a head-mountable display system comprising a frame to be mounted onto an observer's head, the frame defining one or two eye display positions which, in use, are positioned in front of a respective eye of the observer and a display element mounted with respect to each of the eye display positions, the display element providing a virtual image of a video display of a video signal from a video signal source to that eye of the observer.

FIG. 1 shows just one example of an HMD. Other formats are possible: for example an HMD could use a frame more similar to that associated with conventional eyeglasses, namely a substantially horizontal leg extending back from the display portion to the top rear of the user's ear, possibly curling down behind the ear. In other (not full immersion) examples, the user's view of the external environment may not in fact be entirely obscured; the displayed images could be arranged so as to be superposed (from the user's point of view) over the external environment. An example of such an arrangement will be described below with reference to FIG. 4.

In the example of FIG. 1, a separate respective display is provided for each of the user's eyes. A schematic plan view of how this is achieved is provided as FIG. 2, which illustrates the positions 100 of the user's eyes and the relative position 110 of the user's nose. The display portion 50, in schematic form, comprises an exterior shield 120 to mask ambient light from the user's eyes and an internal shield 130 which prevents one eye from seeing the display intended for the other eye. The combination of the user's face, the exterior shield 120 and the interior shield 130 form two compartments 140, one for each eye. In each of the compartments there is provided a display element 150 and one or more optical elements 160. The way in which the display element and the optical element(s) cooperate to provide a display to the user will be described with reference to FIG. 3.

Figure 3:
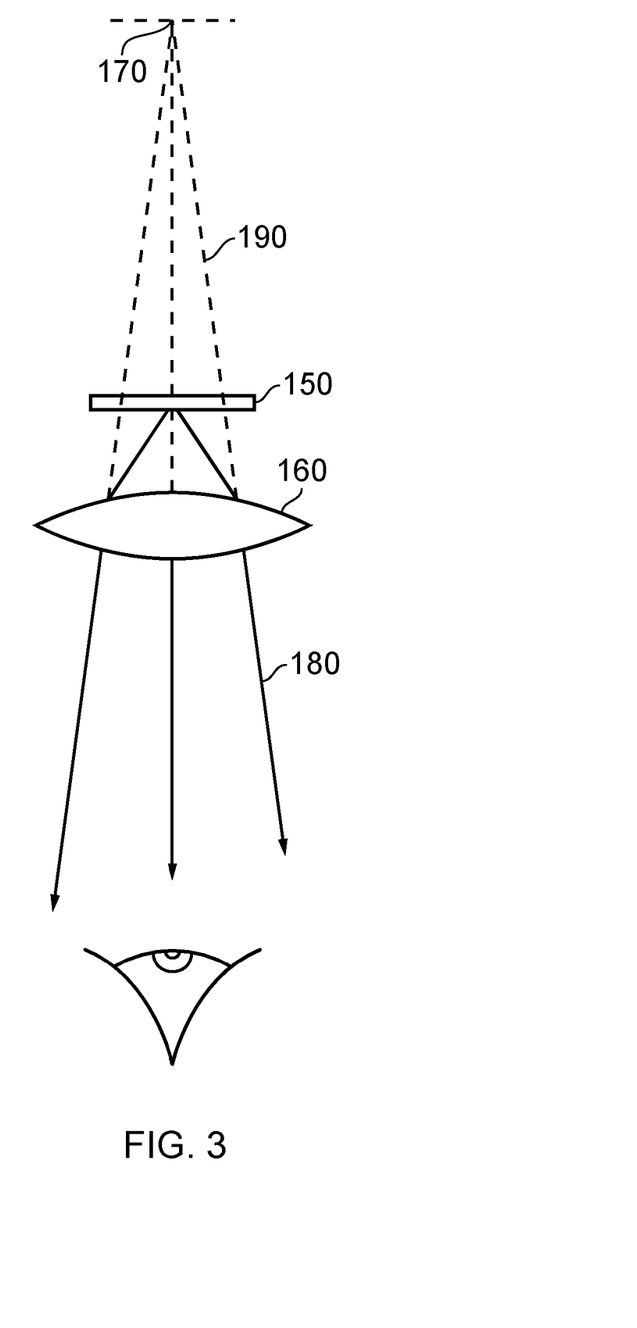
FIG. 3 schematically illustrates the formation of a virtual image by an HMD.

Referring to FIG. 3, the display element 150 generates a displayed image which is (in this example) refracted by the optical elements 160 (shown schematically as a convex lens but which could include compound lenses or other elements) so as to generate a virtual image 170 which appears to the user to be larger than and significantly further away than the real image generated by the display element 150. As an example, the virtual image may have an apparent image size (image diagonal) of more than 1 m and may be disposed at a distance of more than 1 m from the user's eye (or from the frame of the HMD). In general terms, depending on the purpose of the HMD, it is desirable to have the virtual image disposed a significant distance from the user. For example, if the HMD is for viewing movies or the like, it is desirable that the user's eyes are relaxed during such viewing, which requires a distance (to the virtual image) of at least several meters. In FIG. 3, solid lines (such as the line 180) are used to denote real optical rays, whereas broken lines (such as the line 190) are used to denote virtual rays.

Figure 4:
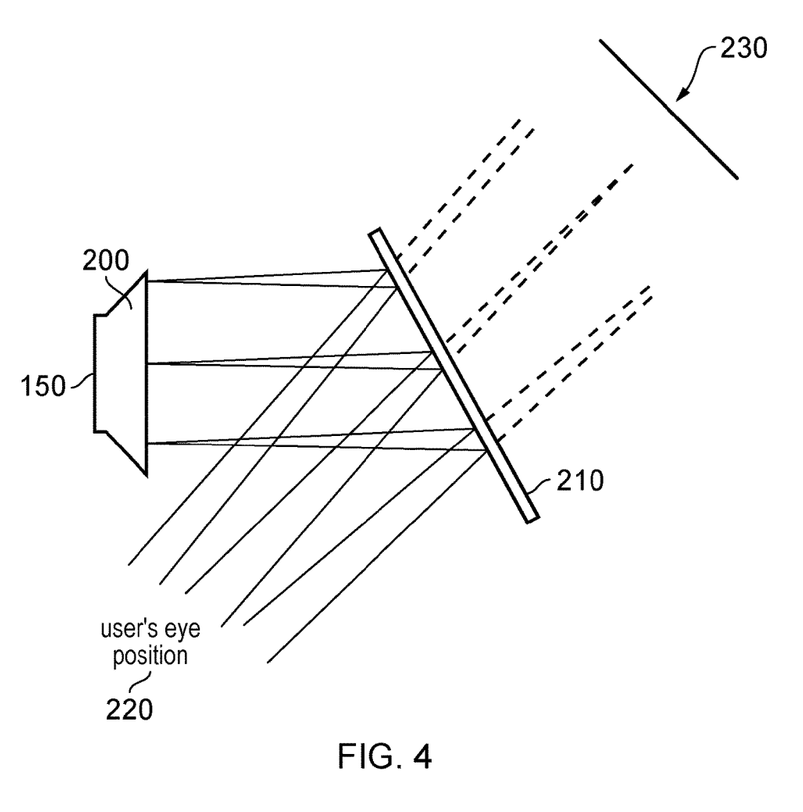
FIG. 4 schematically illustrates another type of display for use in an HMD.

An alternative arrangement is shown in FIG. 4. This arrangement may be used where it is desired that the user's view of the external environment is not entirely obscured. However, it is also applicable to HMDs in which the user's external view is wholly obscured. In the arrangement of FIG. 4, the display element 150 and optical elements 200 cooperate to provide an image which is projected onto a mirror 210, which deflects the image towards the user's eye position 220. The user perceives a virtual image to be located at a position 230 which is in front of the user and at a suitable distance from the user.

In the case of an HMD in which the user's view of the external surroundings is entirely obscured, the mirror 210 can be a substantially 100% reflective mirror. The arrangement of FIG. 4 then has the advantage that the display element and optical elements can be located closer to the centre of gravity of the user's head and to the side of the user's eyes, which can produce a less bulky HMD for the user to wear. Alternatively, if the HMD is designed not to completely obscure the user's view of the external environment, the mirror 210 can be made partially reflective so that the user sees the external environment, through the mirror 210, with the virtual image superposed over the real external environment.

Figure 5:
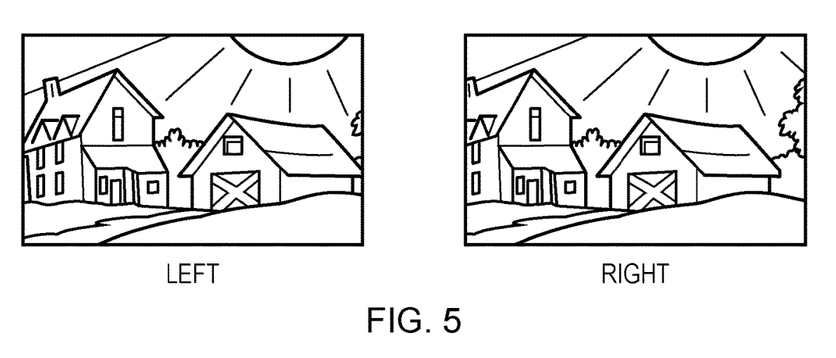
FIG. 5 schematically illustrates a pair of stereoscopic images.

In the case where separate respective displays are provided for each of the user's eyes, it is possible to display stereoscopic images. An example of a pair of stereoscopic images for display to the left and right eyes is shown in FIG. 5. The images exhibit a lateral displacement relative to one another, with the displacement of image features depending upon the (real or simulated) lateral separation of the cameras by which the images were captured, the angular convergence of the cameras and the (real or simulated) distance of each image feature from the camera position.

Note that the lateral displacements in FIG. 5 could in fact be the other way round, which is to say that the left eye image as drawn could in fact be the right eye image, and the right eye image as drawn could in fact be the left eye image. This is because some stereoscopic displays tend to shift objects to the right in the right eye image and to the left in the left eye image, so as to simulate the idea that the user is looking through a stereoscopic window onto the scene beyond. However, some HMDs use the arrangement shown in FIG. 5 because this gives the impression to the user that the user is viewing the scene through a pair of binoculars. The choice between these two arrangements is at the discretion of the system designer.

In some situations, an HMD may be used simply to view movies and the like. In this case, there is no change required to the apparent viewpoint of the displayed images as the user turns the user's head, for example from side to side. In other uses, however, such as those associated with virtual reality (VR) or augmented reality (AR) systems, the user's viewpoint needs to track movements with respect to a real or virtual space in which the user is located.

Figure 6:
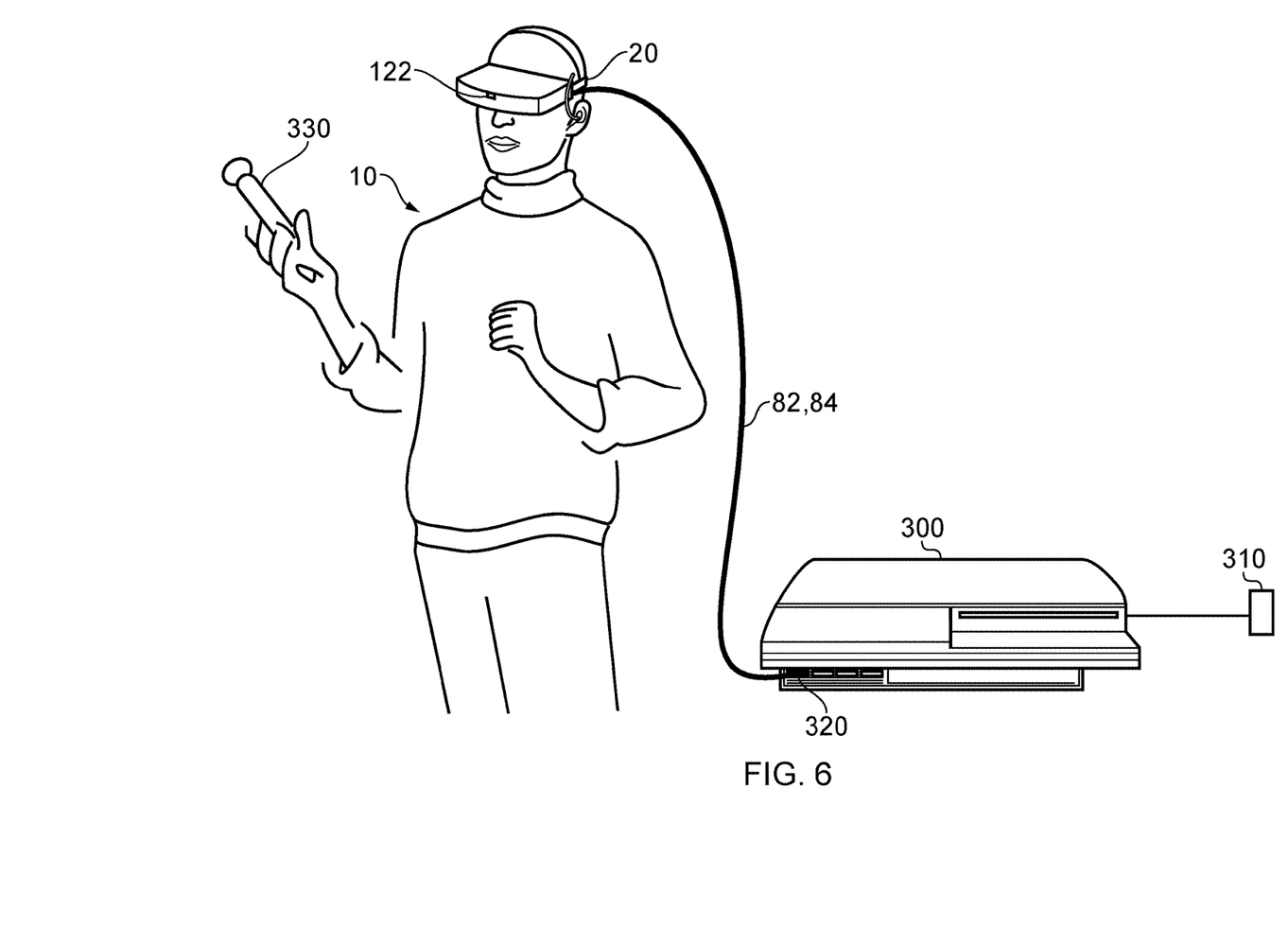
FIGS. 6 and 7 schematically illustrate a user wearing an HMD connected to a Sony® PlayStation 3® games console.

FIG. 6 schematically illustrates a user wearing an HMD connected to a Sony® PlayStation 3® games console 300 as an example of a base device. The games console 300 is connected to a mains power supply 310 and (optionally) to a main display screen (not shown). A cable, acting as the cables 82, 84 discussed above (and so acting as both power supply and signal cables), links the HMD 20 to the games console 300 and is, for example, plugged into a USB socket 320 on the console 300. Note that in the present embodiments, a single physical cable is provided which fulfils the functions of the cables 82, 84. In FIG. 6, the user is also shown holding a hand-held controller 330 which may be, for example, a Sony® Move® controller which communicates wirelessly with the games console 300 to control (or to contribute to the control of) game operations relating to a currently executed game program.

The video displays in the HMD 20 are arranged to display images generated by the games console 300, and the earpieces 60 in the HMD 20 are arranged to reproduce audio signals generated by the games console 300. Note that if a USB type cable is used, these signals will be in digital form when they reach the HMD 20, such that the HMD 20 comprises a digital to analogue converter (DAC) to convert at least the audio signals back into an analogue form for reproduction.

Images from the camera 122 mounted on the HMD 20 are passed back to the games console 300 via the cable 82, 84. Similarly, if motion or other sensors are provided at the HMD 20, signals from those sensors may be at least partially processed at the HMD 20 and/or may be at least partially processed at the games console 300. The use and processing of such signals will be described further below.

The USB connection from the games console 300 also provides power to the HMD 20, according to the USB standard.

Figure 7:
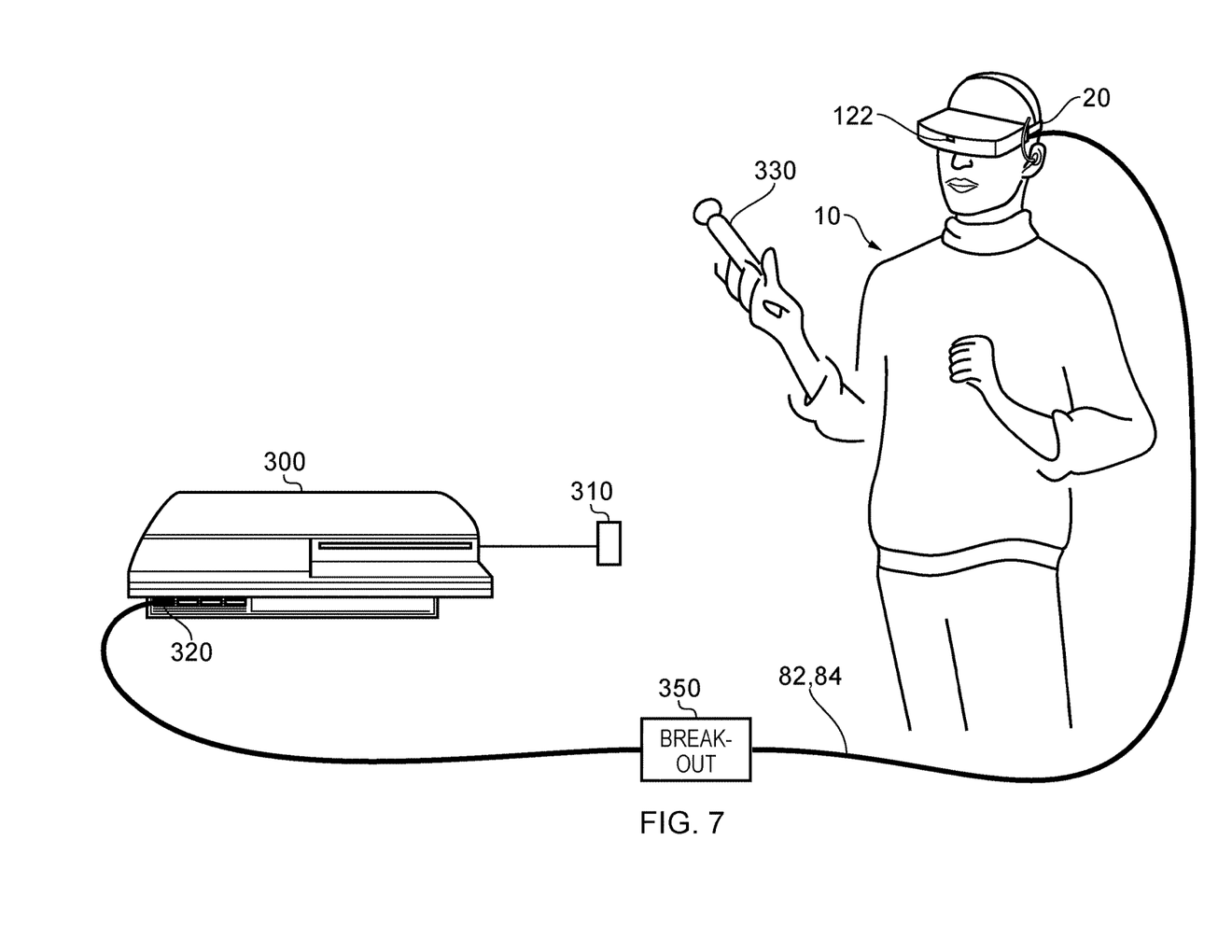

FIG. 7 schematically illustrates a similar arrangement in which the games console is connected (by a wired or wireless link) to a so-called "break out box" acting as a base or intermediate device 350, to which the HMD 20 is connected by a cabled link 82,84. The breakout box has various functions in this regard. One function is to provide a location, near to the user, for some user controls relating to the operation of the HMD, such as (for example) one or more of a power control, a brightness control, an input source selector, a volume control and the like. Another function is to provide a local power supply for the HMD (if one is needed according to the embodiment being discussed). Another function is to provide a local cable anchoring point. In this last function, it is not envisaged that the break-out box 350 is fixed to the ground or to a piece of furniture, but rather than having a very long trailing cable from the games console 300, the break-out box provides a locally weighted point so that the cable 82, 84 linking the HMD 20 to the break-out box will tend to move around the position of the break-out box. This can improve user safety and comfort by avoiding the use of very long trailing cables.

It will be appreciated that the localisation of processing in the various techniques described in this application can be varied without changing the overall effect, given that an HMD may form part of a set or cohort of interconnected devices (that is to say, interconnected for the purposes of data or signal transfer, but not necessarily connected by a physical cable). So, processing which is described as taking place "at" one device, such as at the HMD, could be devolved to another device such as the games console (base device) or the break-out box. Processing tasks can be shared amongst devices. Source signals, on which the processing is to take place, could be distributed to another device, or the processing results from the processing of those source signals could be sent to another device, as required. So any references to processing taking place at a particular device should be understood in this context. Similarly, where an interaction between two devices is basically symmetrical, for example where a camera or sensor on one device detects a signal or feature of the other device, it will be understood that unless the context prohibits this, the two devices could be interchanged without any loss of functionality.

As mentioned above, in some uses of the HMD, such as those associated with virtual reality (VR) or augmented reality (AR) systems, the user's viewpoint needs to track movements with respect to a real or virtual space in which the user is located.

This tracking is carried out by detecting motion of the HMD and varying the apparent viewpoint of the displayed images so that the apparent viewpoint tracks the motion.

Figure 8:
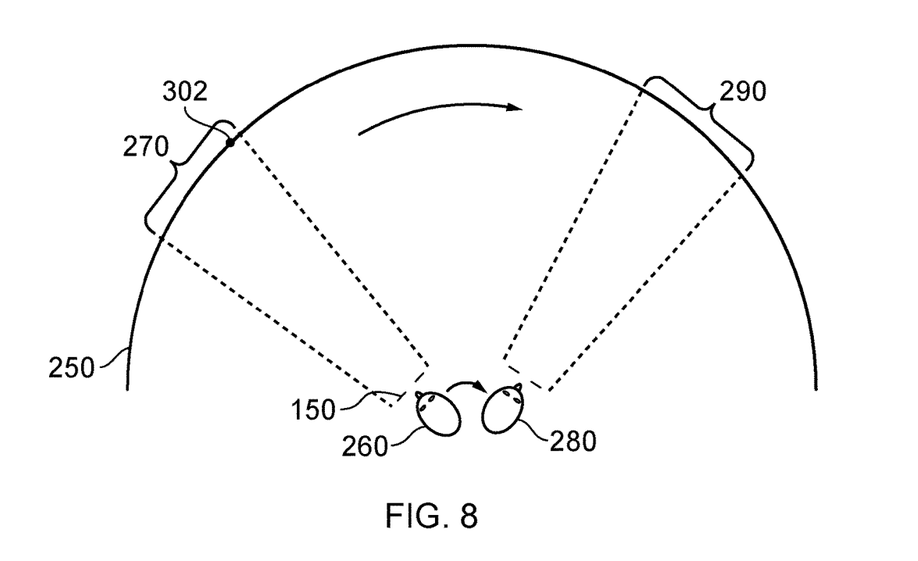
FIG. 8 schematically illustrates a change of view of user of an HMD.

FIG. 8 schematically illustrates the effect of a user head movement in a VR or AR system.

Referring to FIG. 8, a virtual environment is represented by a (virtual) spherical shell 250 around a user. Because of the need to represent this arrangement on a two-dimensional paper drawing, the shell is represented by a part of a circle, at a distance from the user equivalent to the separation of the displayed virtual image from the user. A user is initially at a first position 260 and is directed towards a portion 270 of the virtual environment. It is this portion 270 which is represented in the images displayed on the display elements 150 of the user's HMD.

Consider the situation in which the user then moves his head to a new position and/or orientation 280. In order to maintain the correct sense of the virtual reality or augmented reality display, the displayed portion of the virtual environment also moves so that, at the end of the movement, a new portion 290 is displayed by the HMD.

So, in this arrangement, the apparent viewpoint within the virtual environment moves with the head movement. If the head rotates to the right side, for example, as shown in FIG. 8, the apparent viewpoint also moves to the right from the user's point of view. If the situation is considered from the aspect of a displayed object, such as a displayed object 300, this will effectively move in the opposite direction to the head movement. So, if the head movement is to the right, the apparent viewpoint moves to the right but an object such as the displayed object 300 which is stationary in the virtual environment will move towards the left of the displayed image and eventually will disappear off the left-hand side of the displayed image, for the simple reason that the displayed portion of the virtual environment has moved to the right whereas the displayed object 300 has not moved in the virtual environment.

Figure 2:
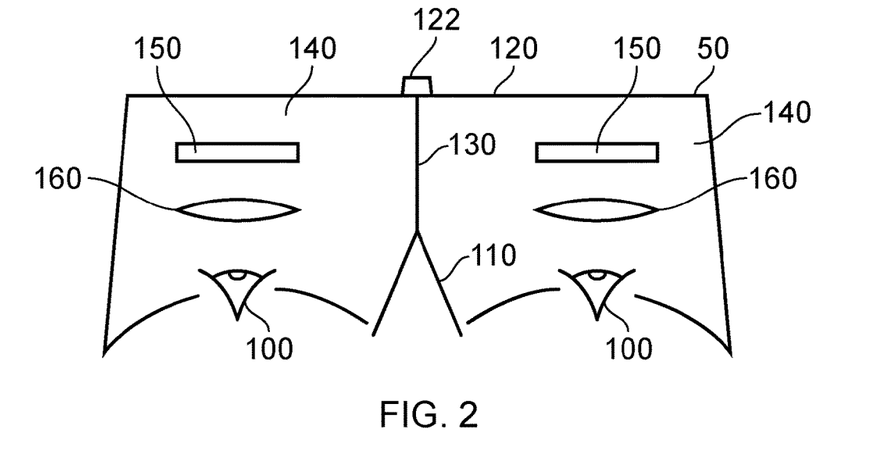
FIG. 2 is a schematic plan view of an HMD.
Figure 9A:
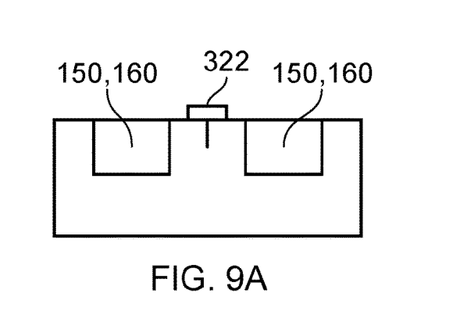
FIGS. 9a and 9b schematically illustrate HMDs with motion sensing.
Figure 9B:
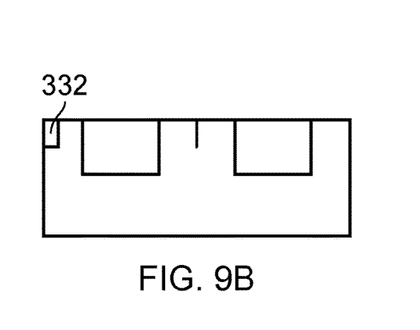

FIGS. 9a and 9b schematically illustrated HMDs with motion sensing. The two drawings are in a similar format to that shown in FIG. 2. That is to say, the drawings are schematic plan views of an HMD, in which the display element 150 and optical elements 160 are represented by a simple box shape. Many features of FIG. 2 are not shown, for clarity of the diagrams. Both drawings show examples of HMDs with a motion detector for detecting motion of the observer's head.

In FIG. 9a, a forward-facing camera 322 is provided on the front of the HMD. This may be the same camera as the camera 122 discussed above, or may be an additional camera. This does not necessarily provide images for display to the user (although it could do so in an augmented reality arrangement). Instead, its primary purpose in the present embodiments is to allow motion sensing. A technique for using images captured by the camera 322 for motion sensing will be described below in connection with FIG. 10. In these arrangements, the motion detector comprises a camera mounted so as to move with the frame; and an image comparator operable to compare successive images captured by the camera so as to detect inter-image motion.

FIG. 9b makes use of a hardware motion detector 332. This can be mounted anywhere within or on the HMD. Examples of suitable hardware motion detectors are piezoelectric accelerometers or optical fibre gyroscopes. It will of course be appreciated that both hardware motion detection and camera-based motion detection can be used in the same device, in which case one sensing arrangement could be used as a backup when the other one is unavailable, or one sensing arrangement (such as the camera) could provide data for changing the apparent viewpoint of the displayed images, whereas the other (such as an accelerometer) could provide data for image stabilisation.

Figure 10:
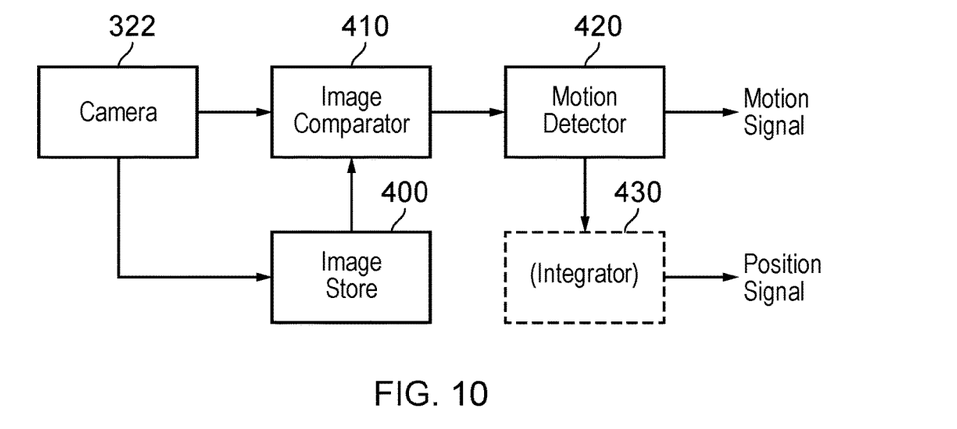
FIG. 10 schematically illustrates a position sensor based on optical flow detection.

FIG. 10 schematically illustrates one example of motion detection using the camera 322 of FIG. 9a.

The camera 322 is a video camera, capturing images at an image capture rate of, for example, 25 images per second. As each image is captured, it is passed to an image store 400 for storage and is also compared, by an image comparator 410, with a preceding image retrieved from the image store. The comparison uses known block matching techniques (so-called "optical flow" detection) to establish whether substantially the whole image has moved since the time at which the preceding image was captured. Localised motion might indicate moving objects within the field of view of the camera 322, but global motion of substantially the whole image would tend to indicate motion of the camera rather than of individual features in the captured scene, and in the present case because the camera is mounted on the HMD, motion of the camera corresponds to motion of the HMD and in turn to motion of the user's head.

The displacement between one image and the next, as detected by the image comparator 410, is converted to a signal indicative of motion by a motion detector 420. If required, the motion signal is converted by to a position signal by an integrator 430.

As mentioned above, as an alternative to, or in addition to, the detection of motion by detecting inter-image motion between images captured by a video camera associated with the HMD, the HMD can detect head motion using a mechanical or solid state detector 332 such as an accelerometer. This can in fact give a faster response in respect of the indication of motion, given that the response time of the video-based system is at best the reciprocal of the image capture rate. In some instances, therefore, the detector 332 can be better suited for use with higher frequency motion detection. However, in other instances, for example if a high image rate camera is used (such as a 200 Hz capture rate camera), a camera-based system may be more appropriate. In terms of FIG. 10, the detector 332 could take the place of the camera 322, the image store 400 and the comparator 410, so as to provide an input directly to the motion detector 420. Or the detector 332 could take the place of the motion detector 420 as well, directly providing an output signal indicative of physical motion.

Other position or motion detecting techniques are of course possible. For example, a mechanical arrangement by which the HMD is linked by a moveable pantograph arm to a fixed point (for example, on a data processing device or on a piece of furniture) may be used, with position and orientation sensors detecting changes in the deflection of the pantograph arm. In other embodiments, a system of one or more transmitters and receivers, mounted on the HMD and on a fixed point, can be used to allow detection of the position and orientation of the HMD by triangulation techniques. For example, the HMD could carry one or more directional transmitters, and an array of receivers associated with known or fixed points could detect the relative signals from the one or more transmitters. Or the transmitters could be fixed and the receivers could be on the HMD. Examples of transmitters and receivers include infra-red transducers, ultrasonic transducers and radio frequency transducers. The radio frequency transducers could have a dual purpose, in that they could also form part of a radio frequency data link to and/or from the HMD, such as a Bluetooth® link.

Figure 11:
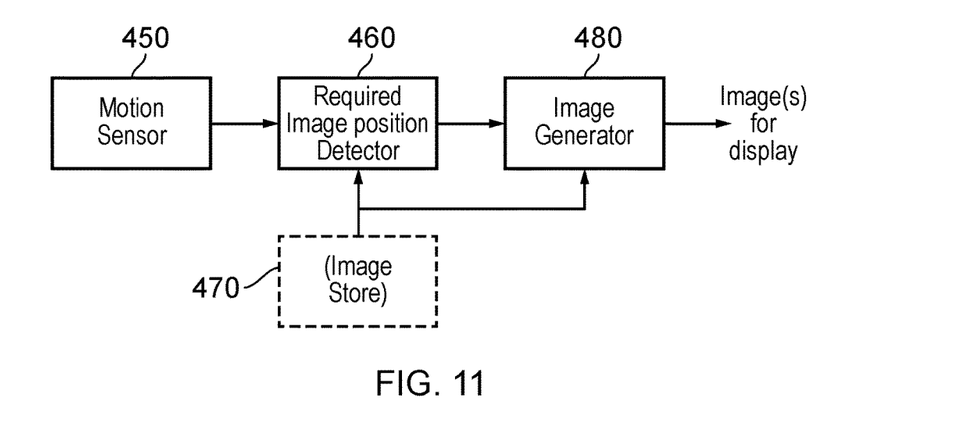
FIG. 11 schematically illustrates the generation of images in response to HMD position or motion detection.

FIG. 11 schematically illustrates image processing carried out in response to a detected position or change in position of the HMD.

As mentioned above in connection with FIG. 10, in some applications such as virtual reality and augmented reality arrangements, the apparent viewpoint of the video being displayed to the user of the HMD is changed in response to a change in actual position or orientation of the user's head.

With reference to FIG. 11, this is achieved by a motion sensor 450 (such as the arrangement of FIG. 10 and/or the motion detector 332 of FIG. 9b) supplying data indicative of motion and/or current position to a required image position detector 460, which translates the actual position of the HMD into data defining the required image for display. An image generator 480 accesses image data stored in an image store 470 if required, and generates the required images from the appropriate viewpoint for display by the HMD. The external video signal source can provide the functionality of the image generator 480 and act as a controller to compensate for the lower frequency component of motion of the observer's head by changing the viewpoint of the displayed image so as to move the displayed image in the opposite direction to that of the detected motion so as to change the apparent viewpoint of the observer in the direction of the detected motion.

The operations to be discussed below relate to the collection of motion data indicative of the type of motion (particularly, head motion) associated with a particular user or a cohort of typical users of an HMD, and varying the execution of a current activity or operation associated with the HMD in dependence upon such motion data.

Some examples of this type arrangement will now be discussed.

In one example, where the HMD is used in a computer gaming context, a gaming product such as a free trial game can be provided to the users. For example, this gaming product might be provided with the HMD as shipped in order to illustrate, to a new user, some of the capabilities of the HMD. As a by-product of the operation of this gaming product, the HMD can detect aspects such as the extent of the available movement for a particular user (for example, how far the current user can comfortably move his neck in each direction) by providing progressively harder actions for the user to follow in order to continue use of the gaming product. Other aspects can be detected such as whether there is any correlation between the amount of head movement required for a particular gaming activity and the length of time for which a user is comfortable to undertake that gaming activity.

Such basic motion data can be acquired by other gaming or video products associated with the HMD, for example during a setup or a calibration stage of a particular data processing product.

The motion data can be stored in respect of a particular user and/or can be aggregated for multiple users, for example by being stored at an Internet server or in cloud-based storage.

Some ways in which the user-specific and/or aggregated motion data can be used in the execution of a data processing gaming system will now be discussed.

If the limits of head motion for which a user (or users in general) are established, these can be applied as limits to the head motion required by a particular product or activity. One way in which this can be done is by applying a scaling or a gearing between the detected head motion of a user and the effect which that had motion has on the operation of the current activity using the HMD. For example, assuming the user (or a typical user) is incapable of moving his head by 180° to the rear, but a gaming activity requires display of items behind the user, the actual extent of free movement by the user can be mapped or scaled to provide a view of the virtual world which is 180° behind the user. So, for example, if a particular user or the typical user can rotate his head by (say) 100° towards the rear, a mapping between the virtual world and real movements of the user's head can be applied so that each successive degree of rotation of the user's head towards the rear is scaled to a rotation in the virtual world of 1.8°.

An acclimatisation period can be used for new users so that the amount of head movement required during operation of a particular activity relating to the HMD varies with time such that during an initial period less movement is required then during a later period of use.

If a particular user is detected to be moving his head in such a way that it is this detected to be excessive with relation to other corresponding users of the same product or activity, for example such that head movements in respect of particular operations are by an angle of rotation which exceeds the typical user's angle of rotation for those activities by a threshold amount or a threshold proportion, then the rotation scaling (see above) for that user can be increased so as to have the effect of reducing the requirements for head motion by that user. For example, a scaling of each degree of real movement corresponding to 2° of movement in the virtual world could be applied.

In any of the above arrangements, the maximum required head movement to operate a particular activity or game associated with the HMD can be capped so as to be less than the available range of head movements for a particular or a typical user, as detected by the motion data discussed above.

In further example arrangements, if the range of head motion carried out by a particular user (for example, in response to a known stimulus such as a particular stage of a game or a predetermined training exercise) is lower than that associated with the stored motion data representing motion by a group of others, then changes can be made or proposed (for the user to accept) to the user display associated with the HMD. The virtual size of the display area could be made smaller so that in order to allow head movement towards different display areas, a smaller range of head movements would be required. If the user's head moves further than the average of other users represented in the stored motion data, then the requirements for head motion to achieve different functionality could be increased.

If little or no head movement is detected, even in response to known stimuli, then eye tracking could be substituted (by the system) for head movement detection, so that functions normally associated with detected head motion are instead associated with detected eye motion.

If the user's head motion is detected to be excessive, random or unconnected with the material being displayed by the HMD, then it could be the case that the user has a lesser degree of motor control than the average other user. Possible measures in response to this detection include one or both of: the system ignoring head movements over a threshold speed or acceleration, or the system setting the size of displayed user interface controls (such as controls operated by the user moving his head to point to that display area) to be larger than those applicable to average or other users.

Figure 12:
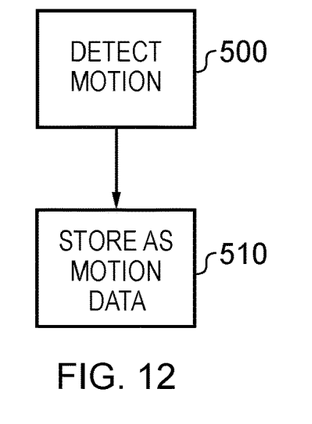
FIG. 12 is a flowchart schematically illustrating part of the operation of an HMD.

FIG. 12 is a flowchart schematically illustrating part of the operation of an HMD by which any or all of the above techniques may be implemented.

At a step 500, had motion associated with use by a particular user of the HMD is detected, and that a step 510, the head motion is stored as motion data. The motion data may be stored locally (in association with that HMD), remotely as part of aggregated or personal user data, or both.

Figure 13:
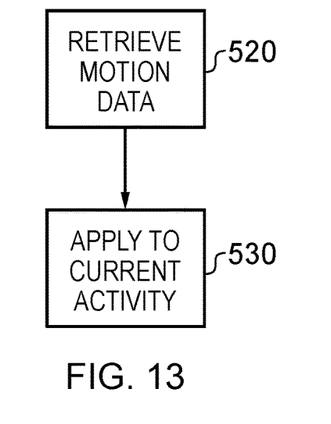
FIG. 13 is a flowchart schematically illustrating part of the operation of an HMD.

FIG. 13 is a flowchart schematically illustrating part of the operation of an HMD in order to make use of the stored motion data. At a step 520, motion data is retrieved either from local storage, or from remote storage, or both. At a step 530, the motion data is applied to the current HMD activity (for example, a gaming activity) according to the principles discussed above.

Figure 14:
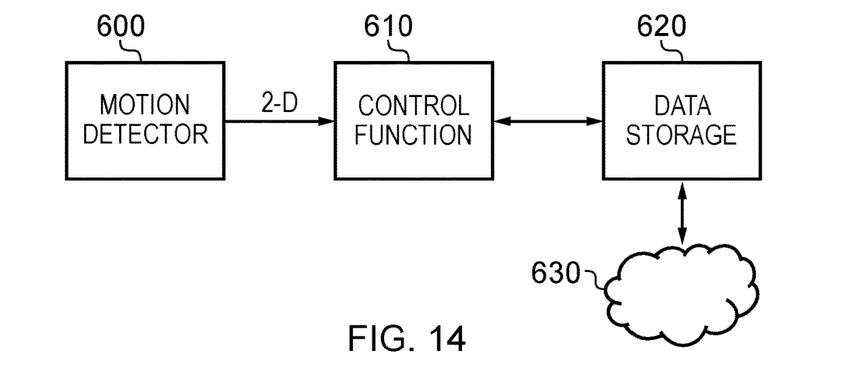
FIG. 14 schematically illustrates a part of an HMD.

FIG. 14 schematically illustrates a part of an HMD of the type discussed earlier. A motion detector 600 detects head motion using the detection techniques discussed earlier. A control function 610 controls operation of the current HMD activity, for example by changing the viewpoint of a game or a video display as discussed earlier, according to the detected motion data. The control function also stores the motion data in data storage 620 which, as discussed above, may be local to the HMD or remote (such as cloud-based storage 630) or both. As a further function, the control function 610 retrieves motion data from the data storage 620, 630 and, using the techniques discussed above, applies it to the current HMD activity. Only one HMD is shown in FIG. 14, but in a practical system there might be plural HMDs connected to the data storage 620, providing an example of a system comprising a set of two or more such HMDs and a data processor (implemented, for example, by the data storage 620 and/or by one of the HMDs or an external device or server) configured to amalgamate motion data from the set of HMDs and to supply the amalgamated motion data to one or more of the HMDs of the set.

Figure 15:
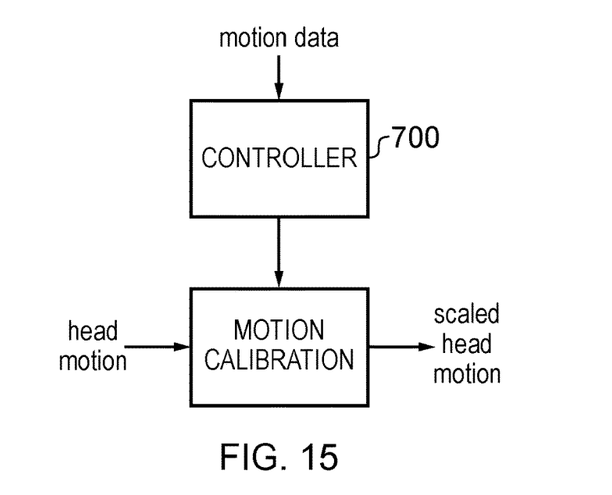
FIG. 15 schematically illustrates a part of an HMD.

FIG. 15 schematically illustrates a part of an HMD specifically relating to a calibration operation of an HMD. A controller 700 receives motion data, for example from the data storage 620, 630, indicative of the maximum range of head motion of a particular user. A motion calibration function 710 applies a scaling factor to currently detected head motion to generate scaled head motion for use in control of a current HMD activity, so that a full range of head motion required by the current HMD activity is scaled from the available range of head motion for the particular user. As discussed above, if the current HMD activity requires a range of head motion of (for example) X degrees of lateral or vertical rotation, but the user is capable of only Y degrees of rotation in that direction, where Y<X, then the calibration function applies a scaling of X/Y to the detected head motion of the user to generate scaled head motion for use in controlling the current HMD activity.

Additionally, or instead of the motion tracking liberation as discussed above, similar techniques can be applied to eye tracking of the user's eye orientation during operation of an HMD. These arrangements will be discussed with reference to FIGS. 16-18 below.

Figure 16:
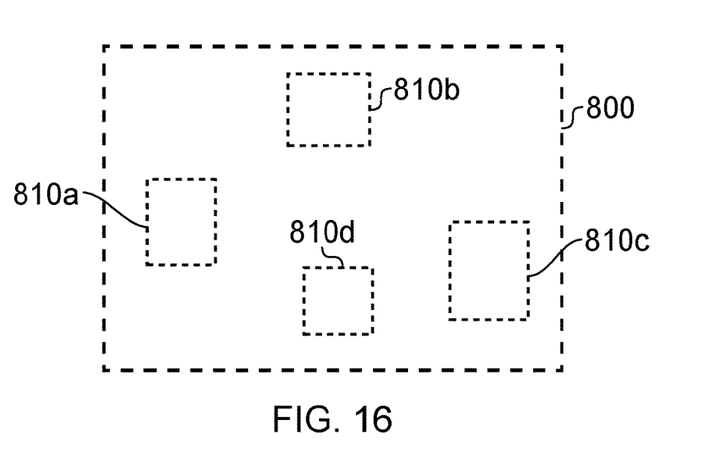
FIG. 16 schematically illustrates a display image.

FIG. 16 schematically illustrates a display image 800. The image may be generated by a rendering unit of a games machine, for example, or it may represent externally supplied video or image data with associated metadata (to be discussed below). In terms of use of the metadata, it is immaterial whether the metadata is generated with the images by a device such as a games machine local to the HMD or whether it is received from an external source with the images. As an example, however, in the case of local generation, metadata could be generated as discussed below.

Within the image 800, there may be so-called regions of interest. For example, these could relate to different game characters being displayed or to advertising features such as virtual billboards or product placements within the image 800. In any of these cases, certain regions 810a, 810b, 810c, 810d are designated by the rendering unit as regions of interest. In some examples, the regions defined by these areas within the display image extend beyond the actual item of interest (the product placement, the game character or the like) so as to provide a margin around that item of interest. This margin allows for any potential inaccuracies in the eye orientation detection to be allowed for by detecting the user's general interest in the area around the item of interest.

Figure 17:
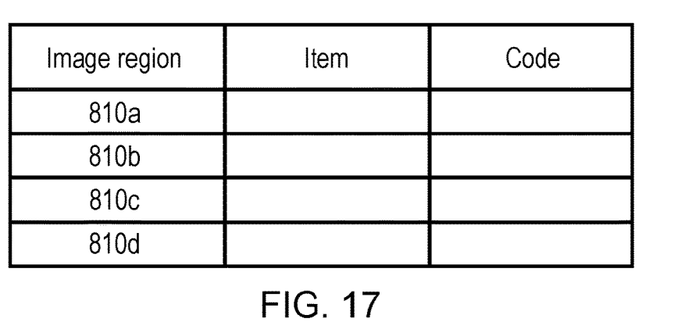
FIG. 17 schematically illustrates an image region table.

FIG. 17 schematically illustrates an image region table, which associates the image regions 810a . . . 810d with an identification of the item concerned and a quasi unique or unique code or reference. Whenever a detection of eye orientation, for example using one or more cameras disposed within the compartments 140 of the HMD and directed towards the user's eyes, indicates that the user's gaze is falling on one of the identified regions of interest, data is recorded associating the item and code associated with that image region with the time period in which the gaze was directed at that image region. Using similar functionality to that discussed with reference to FIG. 14, a collective set of data relating to multiple users can be assembled, for example using a cloud storage provider, to detect regions of interest within images, and associated items and codes, across a more statistically appropriate sample size than that provided by a single user. Accordingly, the areas in a game or other displayed material which a community of users likes to observe in preference to other image regions can be detected. Of course, the discussion so far relates only to the technology underlying this feature. In practical situations, though not relevant to the claims of the present application, privacy would be an important aspect, such that a user's permission would normally be required before this type of gaze detection data was amalgamated with other data to provide an average or community based gaze preference analysis.

As mentioned, instead of game related data generated locally, the image 800 could represent a panoramic view of a geographical area such that geographical areas of interest can be identified by the community-based analysis discussed above, or a television programme so that different characters or presenters of interest can be identified in this manner. Various other possibilities will be apparent to the skilled person reading this description.

Figure 18:
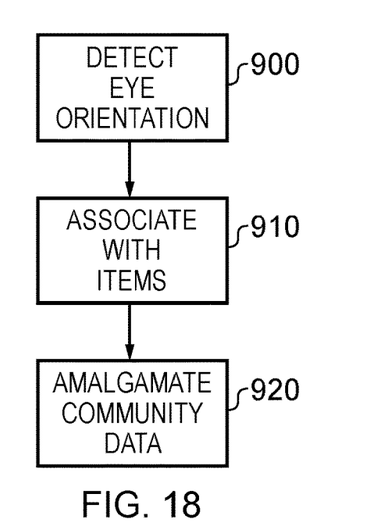
FIG. 18 is a schematic flowchart illustrating techniques for noting eye orientation.

FIG. 18 is a schematic flowchart illustrating techniques for noting eye orientation. At a step 900, the eye orientation of the HMD where it is detected, as discussed above. At step 910, the detected by orientation is associated with regions and items of interest within the currently displayed image. At a step 920, this data is amalgamated with data from other users to form amalgamated community data in the manner discussed above. This provides an example of the operation of a system comprising a set of two or more such HMDs and a data processor (for example, being implemented by one of the HMDs or an external server) configured to amalgamate item data from the set of HMDs.

Accordingly, embodiments of the invention can provide a head mountable display (HMD) having a head motion detection function and one or more operations which depend upon detected head motion, in which detected head motion is stored as motion data (and optionally aggregated with motion data for other users), and in which the way in which detected head motion is applied to a current operation depends upon the stored motion data.

Embodiments of the invention provide for scaling between the available range of head motion for a particular user and the range of head motion required by a particular HMD activity.

Embodiments of the invention provide a system in which an HMD activity is arranged to require less head motion during an initial period of use than during a later period of use of the same HMD activity.

Embodiments of the invention provide an HMD in which, if head motion unconnected with displayed stimuli is detected, the HMD is operable to disregard head motion over a threshold speed or acceleration.

Embodiments of the invention provide an HMD operable to render user interface controls in a larger format in response to a detection of head motion unconnected with displayed stimuli.

Embodiments of the invention provide an HMD in which, if no head motion greater than a predetermined range of motion is detected, the HMD is operable to detect eye motion of the user and to use the detected eye motion to control the HMD in place of detected head motion.

Embodiments of the invention also provide a system comprising an HMD and one or more of a base device such as a games console and an intermediate device such as a break-out box.

Embodiments of the invention can also provide a method of operation of a head mountable display (HMD) having a head motion detection function and one or more operations which depend upon detected head motion, the method comprising storing detected head motion as motion data (and optionally aggregated with motion data for other users), and applying detected head motion a current operation in dependence upon the stored motion data.

Embodiments of the invention can also provide a method of operation of a head mountable display (HMD) comprising adjusting operation of the HMD so that an HMD activity is arranged to require less head motion during an initial period of use than during a later period of use of the same HMD activity.

It will be appreciated that the various techniques described above may be carried out using software, hardware, software programmable hardware or combinations of these. It will be appreciated that such software, and a providing medium by which such software is provided (such as a machine-readable non-transitory storage medium, for example a magnetic or optical disc or a non-volatile memory) are considered as embodiments of the present invention.

Obviously, numerous modifications and variations of the present disclosure are possible in light of the above teachings. It is therefore to be understood that within the scope of the appended claims, the invention may be practised otherwise than as specifically described herein.

The invention claimed is:

1. A head mountable display (HMD), comprising:
    a frame adapted to hold the HMD on a user's head; and
    one or more display devices coupled to the frame;
    wherein the HMD is configured to perform a head motion detection function and one or more HMD operations which depend upon detected head motion and to store a first head motion associated with use by the user in memory as first motion data,
    wherein the HMD comprises control circuitry to retrieve previously stored motion data from the memory and to apply retrieved first motion data from a previous HMD activity so that a way in which a second, current, detected head motion is applied to a current one of the one or more operations depends upon the stored and retrieved first motion data.

2. An HMD according to claim 1, in which the first motion data comprises data dependent upon the first head motion of the user of the HMD aggregated with motion data for other users.

3. An HMD according to claim 1, wherein the HMD is configured to apply a scaling between an available range of head motion for a particular user and a range of head motion required by a particular one of the one or more HMD operations.

4. An HMD according to claim 1, in which a given one of the one or more HMD operations is arranged to require less head motion during an initial period of use than during a later period of use of the given HMD operation.

5. An HMD according to claim 1, in which, when head motion unconnected with displayed stimuli is detected, the HMD is configured to disregard head motion over a threshold speed or acceleration.

6. An HMD according to claim 5, in which the HMD is configured to render user interface controls in a larger format in response to a detection of head motion unconnected with displayed stimuli.

7. An HMD according to claim 1, in which, when no head motion greater than a predetermined range of motion is detected, the HMD is configured to detect eye motion of the user and to use the detected eye motion to control the HMD in place of detected head motion.

8. An HMD according to claim 1, further comprising:
    a gaze detector configured to detect eye orientation of a user of the user so as to detect image regions at which the user is looking; and
    a detector configured to detect item data indicative of items represented by the detected image regions.

9. A system, comprising:
a set of two or more head mountable displays (HMDs), each HMD comprising:
- a frame adapted to hold the HMD on a user's head; and one or more display devices coupled to the frame;
- wherein the HMD is configured to perform a head motion detection function and one or more HMD operations that depend upon detected head motion and to store a first head motion associated with use by the user in memory as first motion data,
- wherein the HMD comprises control circuitry to retrieve previously stored motion data from the memory and to apply retrieved first motion data from a previous HMD activity so that a way in which a second, current, detected head motion is applied to a current one of the one or more operations depends upon the stored and retrieved first motion data, each HMD comprising:
  - a gaze detector configured to detect eye orientation of a user of the user so as to detect image regions at which the user is looking; and
  - a detector configured to detect item data indicative of items represented by the detected image regions; and
- a data processor operatively coupled to each HMD of the set, the data processor being configured to amalgamate the item data from the set of HMDs.

10. A system, comprising:
a set of two or more head mountable displays (HMDs), each HMD comprising:
- a frame adapted to hold the HMD on a user's head; and one or more display devices coupled to the frame;
- wherein the HMD is configured to perform a head motion detection function and one or more HMD operations that depend upon detected head motion and to store a first head motion associated with use by the user in memory as first motion data,
- wherein the HMD comprises control circuitry to retrieve previously stored motion data from the memory and to apply retrieved first motion data from a previous HMD activity so that a way in which a second, current, detected head motion is applied to a current one of the one or more operations depends upon the stored and retrieved first motion data, wherein the first motion data comprises data dependent upon the first head motion of a user of the HMD aggregated with motion data for other users; and
- a data processor operatively coupled to each HMD of the set, the data processor being configured to amalgamate motion data from the set of HMDs and to supply the amalgamated motion data to one or more of the HMDs of the set.

11. A system, comprising:
an HMD including:
- a frame adapted to hold the HMD on a user's head; and one or more display devices coupled to the frame;
- wherein the HMD is configured to perform a head motion detection function and one or more HMD operations which depend upon detected head motion and to store a first head motion associated with use by the user in memory as first motion data,
- wherein the HMD comprises control circuitry to retrieve previously stored motion data from the memory and to apply retrieved first motion data from a previous HMD activity so that a way in which a second, current, detected head motion is applied to a current one of the one or more operations depends upon the stored and retrieved first motion data; and
- one or more of a base device and an intermediate device operatively coupled to the HMD.

12. A method of operation of a head mountable display (HMD) having a head motion detection function and one or more operations which depend upon detected head motion, the method comprising:
- storing a first detected head motion associated with use by a user as first motion data in memory;
- retrieving previously stored first motion data from the memory; and
- applying, by one or more processing devices, a second, current, detected head motion to a current operation in dependence upon the stored and retrieved first motion data.

13. A non-transitory machine-readable storage medium having instructions stored thereon, the instructions, when executed by one or more processing devices, cause the one or more processing devices to perform a method of operating a head mountable display (HMD) having a head motion detection function and one or more operations that depend upon detected head motion, the method comprising:
- storing a first detected head motion associated with use by a user as first motion data in memory;
- retrieving previously stored first motion data from the memory; and
- applying a second, current, detected head motion to a current operation in dependence upon the stored and retrieved first motion data.

14. A system according to claim 9, in which the first motion data comprises data dependent upon the first head motion of the user of the HMD aggregated with motion data for other users.

15. A system according to claim 10, in which the first motion data comprises data dependent upon the first head motion of the user of the HMD aggregated with motion data for other users.

16. A system according to claim 11, in which the first motion data comprises data dependent upon the first head motion of the user of the HMD aggregated with motion data for other users.

17. A method according to claim 12, in which the first motion data comprises data dependent upon the first detected head motion of the user of the HMD aggregated with motion data for other users.

18. A non-transitory machine-readable storage medium according to claim 13, in which the first motion data comprises data dependent upon the first detected head motion of the user of the HMD aggregated with motion data for other users.

* * * * *